United States Patent
Campbell

(12) 
(10) Patent No.: US 6,559,186 B1
(45) Date of Patent: May 6, 2003

(54) COMPOSITIONS AND METHODS OF TREATMENT OF SYMPATHETICALLY MAINTAINED PAIN

(75) Inventor: James N. Campbell, Lutherville, MD (US)

(73) Assignee: Arc 1, Inc., Lutherville, MD (US)

( * ) Notice: Subject to any disclaimer, the term of this patent is extended or adjusted under 35 U.S.C. 154(b) by 0 days.

(21) Appl. No.: 08/286,404

(22) Filed: Aug. 5, 1994

Related U.S. Application Data

(63) Continuation of application No. 07/747,635, filed on Aug. 20, 1991, now abandoned, which is a continuation-in-part of application No. 07/661,554, filed on Feb. 26, 1991, now abandoned, which is a continuation-in-part of application No. 07/485,156, filed on Feb. 26, 1990, now Pat. No. 5,070,084.

(51) Int. Cl.[7] ........................ A61P 29/00; A61K 31/155; A61K 31/4965; A61K 31/14

(52) U.S. Cl. .............. 514/634; 514/252.12; 514/252.13; 514/252.17; 514/252.19; 514/253.03; 514/253.04; 514/253.05; 514/254.09; 514/310; 514/354; 514/410; 514/462; 514/562; 514/643; 514/651; 514/654; 514/655

(58) Field of Search ................................ 514/401, 402, 514/392, 269, 272, 274, 634, 252.13, 252.12, 252.17, 252.19, 253.04–253.06, 254.09, 310, 354, 462, 643, 651, 654–655, 562, 410, 253.03

(56) References Cited

U.S. PATENT DOCUMENTS

| | | | |
|---|---|---|---|
| 4,201,211 A | | 5/1980 | Chandrasekaran et al. |
| 4,250,191 A | | 2/1981 | Edwards |
| 4,310,535 A | | 1/1982 | Pierpaoli |
| 4,443,441 A | | 4/1984 | Galin |
| 4,557,934 A | * | 12/1985 | Cooper |
| 4,742,054 A | | 5/1988 | Naftchi |
| 4,801,587 A | | 1/1989 | Voss et al. |
| 5,447,947 A | * | 9/1995 | Campbell ................ 514/392 |

FOREIGN PATENT DOCUMENTS

DE  2920500 A1 * 11/1980

OTHER PUBLICATIONS

Olin, B.R. et al., "Facts and Comparisons," J.B. Lipincott Co., St. Louis, Mo., p. 162e, Jan. 1988.*
Goodman Gilman et al., The Pharmacological Basis of Therapeutics (6th Edition), Chapter 9, New York, Mac-Millan, 1980, pp. 176–210.*
Janig, W., Trends in NeuroSciences 8(11), 471–77 (1985).
Loh, L., et al., J. Neurol. Neurosurg. Psychiat. 41(7), 664–71 (1978).
Naftchi, N., Chem. Abst. 110(9):69410r, 1980.
Nakagawa, et al., *Chem. Abstr.* 111(2):12526z.
Nakagawa, et al., *Chem. Abstr.* 110(12):101838z.
Gonzales, et al., *J. Neurochem.* 53(5), 1595–98 (1989).
Hobelman, et al., *Microsurg.* 10(2), 151–53 (1989).
Price, et al., *Pain* 36(3), 273–88 (1989).
Curtis and Marwah, "Evidence for Alpha Adrenoceptor Modulation of the Nociceptive Jaw–Opening Reflex in Rats and Rabbits" *J. Pharmacology Experimental Therapeutics* 238, 576–579 (Aug. 1988).
Sagen and Proudfit, "Evidence for Pain Modulation by Pre– and Postsynaptic Noradrenergic Receptors in the Medulla Oblongata" *Brain Research* 331, 285–293 (1985).
M. Ishizuki, Letter to the Editor, "Clinical Application of Guanethidine Ointment to the Treatment of Painful States and Allodynia" *Clinical Journal of Pain* 261 (1988).

* cited by examiner

Primary Examiner—Edward J. Webman
(74) Attorney, Agent, or Firm—Holland & Knight LLP

(57) ABSTRACT

Sympathetically maintained pain is treated topically by administering to the site where sympathetically maintained pain is present an α-1-adrenergic antagonist, α-2-adrenergic agonist, or other drug that depletes or blocks synthesis of sympathetic norepinephrine, known collectively as sympatholytic agents. Chemical formulas for several sympatholytic agents are given.

12 Claims, No Drawings

COMPOSITIONS AND METHODS OF TREATMENT OF SYMPATHETICALLY MAINTAINED PAIN

This is a continuation of application U.S. Ser. No. 07/747,635 entitled "Compositions and Methods of Treatment of Sympathetically Maintained Pain" filed Aug. 20, 1991 by James N. Campbell, now abandoned, which is a continuation-in-part of U.S. Ser. No. 07/661,554 entitled "Compositions and Methods of Treatment of Sympathetically,Maintained Pain" filed Feb. 26, 1991, now abandoned, which is a continuation-in-part of U.S. Ser. No. 07/485,156 entitled "Diagnosis and Treatment of Sympathetically Maintained Pain" filed Feb. 26, 1990, now U.S. Pat. No. 5,070,084.

BACKGROUND OF THE INVENTION

The invention relates to the diagnosis and treatment of sympathetically maintained pain using sympatholytic agents which are defined herein as compounds that interfere with sympathetic function in the peripheral tissue or interfere with the action of drugs associated with sympathetic function.

Several chronic, non-malignant pain syndromes such as causalgia and reflex sympathetic dystrophy have one feature in common: blockade of the sympathetic innervation of the affected body region can lead to pain relief. The pain may result from skeletal, soft tissue, or nerve injury. Terms such as reflex sympathetic dystrophy, Sudek's atrophy, and causalgia have all been used to refer to such patients. The term "sympathetically maintained pain" ("SMP") encompasses all pain syndromes that can be relieved by sympathetic blockade.

Patients with SMP typically have both stimulus-independent (ongoing) pain and stimulus-dependent pain (hyperalgesia). Hyperalgesia is defined as a leftward shift of the stimulus-response function, such that a lowering of pain threshold and/or an increase in pain to suprathreshold stimuli is observed. The decrease in pain threshold to mechanical stimuli may be such that lightly stroking the skin evokes pain, a phenomenon sometimes referred to as allodynia.

Conventional treatments for SMP include repeated local anesthetic sympathetic blocks, intravenous regional guanethidine/reserpine blocks, surgical sympathectomy, or oral sympatholytic therapy. However, each of these treatments carries with it a degree of risk, side effects and discomfort.

One method of diagnosis of SMP is by assessment of the results of a local anesthetic blockade of the sympathetic ganglia (LABSG) that innervate the painful part. Because of the technical expertise required in the performance of the LABSG and the potential complications associated with the LASB, alternate tests for the diagnosis of SMP have been studied. For example, intravenous regional blockage (IVRB) of sympathetic function with guanethidine has been used as a means for the diagnosis and treatment of SMP.

There are several potential disadvantages to the use of LABSG and IVRB. LABSG is subject to false negative results if the local anesthetic fails to anesthetize adequately the sympathetic ganglia. The anesthetic may reach the somatic afferents in the nearby nerve roots and produce pain relief because of concurrent somatic blockade, and certain afferents may in addition course with sympathetic efferents. Certain patients tolerate poorly the application of the tourniquet required with IVRB. LABSG involves strategic localization of the needle prior to injection, and thus fluoroscopy is often needed. With IVRB, the guanethidine may escape into the systemic circulation with resultant systemic untoward effects. A series of complications have been reported with LABSG, including pneumothorax, injury to the kidney, inadvertent systemic application, spinal anesthesia, hemorrhage, etc. It is difficult to evaluate placebo responses with both LABSG and IVRB.

It would therefore be advantageous to have a method of diagnosis and treatment that does not exhibit these difficulties.

Several lines of evidence suggest that peripheral adrenergic receptors are involved in SMP. Stimulation of the peripheral but not central cut end of the sympathetic chain reproduces pain in causalgia patients after sympathectomy. Local anesthetic blockade of the appropriate sympathetic ganglion or adrenergic blockade via intravenous administration of phentolamine, rapidly abolishes sympathetically-maintained pain and hyperalgesia. Depletion of peripheral catecholamines by regional intravenous guanethidine relieves pain and hyperalgesia. Intradermal injection of norepinephrine rekindles the pain and hyperalgesia that had been relieved in patients by sympathectomy or sympathetic block but does not cause pain or hyperalgesia in normal subjects. The non-specific α-adrenergic antagonist phenoxybenzamine and the specific $α_1$-adrenergic antagonist prazosin can be effective in relieving pain in patients with SMP. The beta-adrenergic antagonist propranolol has little effect on SMP.

It is therefore possible that administration of an α-adrenergic blocking agent could be beneficial in the treatment of SMP patients. Therapeutic uses of the α-adrenergic compounds, for example, phentolamine and clonidine, are known in the art. For example, U.S. Pat. No. 4,801,587 discloses the use of phentolamine as a vasodilator to treat impotence. U.S. Pat. No. 4,310,535 discloses the use of phentolamine in combination with other drugs for use in the control of immune reactions. The use of phentolamine and clonidine for controlling hypertension is disclosed in U.S. Pat. No. 4,250,191. α-Adrenergic drugs have been found to be useful in the stabilization of intraocular lenses, as disclosed in U.S. Pat. No. 4,443,441. U.S. Pat. No. 4,201,211, discloses the use of a clonidine patch for therapeutic use as a stimulant for the central nervous system.

It is therefore an object of the present invention to provide a topical method of diagnosis for sympathetically maintained pain that has a low incidence of false positives and false negatives.

It is another object of the present invention to provide a topical method of diagnosis and treatment of sympathetically maintained pain that has a low incidence of adverse reactions with relatively minor complications.

SUMMARY OF THE INVENTION

Sympathetically maintained pain is treated topically by administering to the site where sympathetically maintained pain is present a sympatholytic agent, such as an α-adrenergic antagonist, $α_1$-adrenergic antagonist, $α_2$ adrenergic agonist, or other drug that depletes or blocks synthesis of norepinephrine from the sympathetic terminals. Specific chemical formulas of sympatholytic agents are disclosed Examples demonstrate relief of pain by application of phentolamine or clonidine.

DETAILED DESCRIPTION OF THE INVENTION

Sympathetic efferent fibers release norepinephrine which in turn activates α-adrenergic receptors. Activation of the α-adrenergic receptors by norepinephrine, either directly or indirectly, excites nociceptors. Activity in the nociceptors then evokes pain and further activity in the sympathetic efferent fibers. This, in turn, results in further discharge of the nociceptors. The goal in therapy is to block the effects of norepinephrine on nociceptors. Topical application to the site where sympathetically maintained pain is present of an α-adrenergic antagonist, $\alpha_1$ adrenergic antagonist, $\alpha_2$ adrenergic agonist, a combination thereof, or other drug that depletes or blocks synthesis of norepinephrine at the sympathetic terminals (collectively referred to herein as "sympatholytic agents") relieves the pain.

Topical application of the sympatholytic agent is also used in the treatment of peripheral vascular diseases characterized by high alpha-adrenergic tone in cutaneous blood vessels, such as frostbite, Raynaud's disease, thrombophlebitis, and spastic peripheral vascular disorders.

The compounds used in the present method are known to those skilled in the art. For example, the various classes of compounds and examples thereof are described in *The Pharmacological Basis of Therapeutics*, 8th Edition, Gill, A. G., T. W. Rall, A. S. Nies, P. Taylor, editors (Pergamon Press, Co., Inc., NY 1990), the teachings of which are incorporated herein.

Several different structural classes of sympatholytic agents have been developed, from which a compound can be selected for use as a topical therapy for sympathetically maintained pain. For example, a class of cyclic amidine compounds from which a suitable sympatholytic agent with alpha-1 adrenoreceptor antagonist activity, alpha-2 adrenoreceptor agonist activity, or both activities combined may be selected can be represented by Formula I:

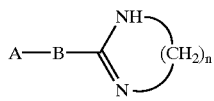

wherein A is selected from aryl, aryloxy, anilino, arylamino, diarylamino, heteroaryl, heteroaryloxy, or heteroarylamino, which may be substituted with one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, oxo, halogen, thioalkyl, dialkylamino, arylamino, alkylsulfinyl, alkylsulfonyl, arylsulfinyl or arylsulfonyl; B may be independently selected from linear alkylene containing from 1 to 4 methylene units, branched alkylene, imino, or thio; and n is either 2 or 3; or a pharmaceutically acceptable salt thereof.

A preferred class of compounds of formula I consists of those compounds wherein A is phenyl, substituted phenyl, phenoxy, substituted phenoxy, naphthyl, tetrahydronaphthyl, or diarylamino; wherein B is methylene or 1-ethylene; and n is 2.

An especially preferred class of compounds of Formula I consists of those compounds wherein A is substituted phenyl, in which positions 2 and 6 of the phenyl ring are substituted by radicals independently selected from hydrido, chloro, methyl, ethyl, cyclopropyl, or thiomethyl, and positions 3, 4, and 5 are substituted by radicals independently selected from hydrido, 2-propyl, tertbutyl; hydroxyl, trifluoromethyl, chloro, or fluoro; and B is methylene, or 1-ethylene when A is substituted phenoxy; and n is 2.

Another especially preferred class of compounds of formula I consists of those compounds wherein A is diarylamino, in which case each aryl group can be independently substituted by hydroxyl; and wherein B is methylene; and n is 2.

Yet another especially preferred class of compounds of Formula-I consists of those compounds wherein A is 1-naphthyl or tetrahydronaphthyl; and B is either zero or one methylene unit; and n is 2.

A family of specifically preferred compounds which are included in Formula I consists of the compounds tetrahydrozoline, naphazoline, phentolamine, dexlofexidine, oxymetazoline, cirazoline, xylometazoline, and tolazidine.

Another class of compounds from which a suitable sympatholytic agent with sympathetic neurotransmitter depleting activity or alpha-1 adrenoreceptor antagonist activity may be selected is that of substituted ureas, represented by Formula II:

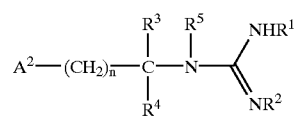

wherein $A^2$ is selected from alkyl, branched alkyl, aryl, aryloxy, heteroaryl, or heterocyclic moiety, which may bear one or more substituents selected from halogen, lower alkyl, aryl, alkoxy, hydroxyl, amino, alkylamino, arylamino, alkylsulfinyl, alkylsulfonyl, arylsulfinyl or arylsulfonyl; wherein $R^1$ and $R^2$ may be independently selected from hydrido, lower alkyl, hydroxyl or cyano; wherein $R^3$ and $R^4$ may be independently selected from hydrido or lower alkyl, or together to form a carbonyl moiety; wherein $R^5$ is selected from hydrido or lower alkyl; and wherein n is any value between 0 and 4 inclusive; or a pharmaceutically acceptable salt thereof.

A preferred class of compounds of Formula II consists of those compounds wherein $A^2$ is selected from lower alkyl, phenyl, substituted phenyl, phenoxy, substituted phenoxy, anilino, substituted anilino, azacyclic, benzodioxan, and substituted dioxolane; wherein $R^1$ is selected from hydrido, methyl, or hydroxyl, and $R^2$ is selected from hydrido or cyano;. wherein $R^3$ and $R^3$ are independently either hydrido or methyl, or together form a carbonyl; wherein $R^5$ is hydrogen; and n is any value from 0 to 3 inclusive.

An especially preferred class of compounds of Formula II consists of those compounds wherein $A^2$ is selected from lower alkyl, 2,6-dichlorophenyl, phenoxy, (2,6-dichloro)phenoxy, (2,6-dichloro)anilino, -4-phenyl-1,2,3,6-tetrahydropyridinyl, octahydro-1-azocinyl, octahydro-2-azocinyl, benzodioxan-2-yl, or 1,4-dioxaspiro[4,5]dec-2-yl; wherein $R^1$ is selected from hydrido, methyl, or hydroxyl, and $R^2$ is selected from hydrido or cyano; wherein $R^3$ and $R^3$ are independently either hydrido or methyl, or together form a carbonyl; wherein $R^5$ is hydrogen; and n is any value from 0 to 3 inclusive.

A family of specifically preferred compounds of Formula II consists of bethanidine, guanfacine, guanclofine, guanoxan, guanethidine, guanazodine, guanoxyfeh, guandcline, guanoctine, and guanadrel.

Another class of compounds from which a suitable sympatholytic agent may be selected with sympathetic neurotransmitter depleting activity, alpha-1 adrenoreceptor antagonist activity, alpha-2 adrenoreceptor agonist activity, or a combination of these actions, is represented by Formula III:

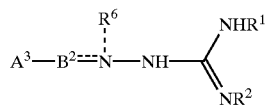

wherein $A^3$ is selected from alkyl, branched alkyl, aryl, aryloxy, heteroaryl, or heterocyclic moiety, which may bear one or more substituents selected from halogen, lower alkyl, aryl, alkoxy, hydroxyl, amino, alkylamino, arylamino, alkylsulfinyl, alkylsulfonyl, arylsulfinyl or arylsulfonyl; $B^2$ is either carbon, wherein it forms an unsaturated imino linkage with the adjacent nitrogen, or linear or branched chain alkylene moiety of 1–4 methylene units in length; $R^1$ and $R^2$ are as defined for Formula II; and $R^6$ is selected from hydrogen or lower alkyl, when the attached nitrogen is not incorporated into an unsaturated imino bond; or a pharmaceutically acceptable salt thereof.

A preferred class of compounds of Formula III consists of those compounds wherein $A^3$ is selected from phenyl or substituted phenyl; wherein $B^2$ is a carbon attached by a double bond to the adjacent nitrogen to form an imino moiety, or where $B^2$ is a saturated linear alkyl chain of 2 methylene units; and wherein $R^1$, $R^2$, and $R^6$ are hydrogen.

An especially preferred class of compounds of Formula III consists those compounds wherein.$A^3$ is a 2,6-disubstituted phenyl moiety, wherein the substituents are selected from chloro or methyl.

A group of specifically preferred compounds of Formula III consists of guanabenz, guanoxabenz, and guanoclor.

Another class of compounds from which a suitable sympatholytic agent with alpha-2 adrenoreceptor agonist activity may be selected is represented by Formula IV:

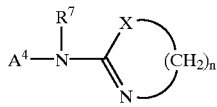

wherein $A^4$ may be selected from aryl, and heteroaryl, which may be substituted by one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, halogen, thioalkyl, dialkylamino, arylamino, alkylsulfinyl, alkylsulfonyl, arylsulfinyl or arylsulfonyl; wherein X is selected from thio, imino, or methylene; wherein $R^7$ is selected from hydrogen, lower alkyl, or oxygen-containing heterocycle; and wherein n is either 2 or 3; or a pharmaceutically acceptable salt thereof.

A preferred class of compounds of Formula IV consists of those compounds wherein $A^4$ is phenyl; wherein $A^4$ is substituted phenyl, on which positions 2 and 6 of the phenyl ring may be independently substituted by a radical selected from hydrogen, chloro, methyl, ethyl, or cycloalkyl, and positions 3, 4, and 5 may be independently substituted by a radical selected from hydrogen, methyl, trifluoromethyl, fluoro, or cyano; wherein $A^4$ is 3-thienyl, on which positions 2 and 4 are independently substituted by a radical selected from hydrogen, chloro, methyl, ethyl, or cycloalkyl; wherein $A^4$ is 1-naphthyl, 5,6,7,8-tetrahydronaphthyl-1-yl, pyrrolyl, oxazolyl, isoxazolyl, indol-3-yl, indazol-3-yl, quinolinyl, quinazolinyl, quinoxazolinyl, benzoxazolyl, and benzothiophen-3-yl; wherein $A^4$ is pyrimidin-4-yl, on which positions 3 and 5 are independently substituted by hydrogen, chloro, methyl, ethyl, cycloalkyl, or methoxy; wherein $R^7$ is either hydrogen or tetrahydropyran-2-yl; wherein X is thio or imino; and wherein n is 2.

An especially preferred class of compounds of Formula IV consists of compounds wherein $A^4$ is selected from phenyl, 2,6-dichlorophenyl, 2,6-dimethylphenyl, 2,6-diethylphenyl, 3,4-dihydroxyphenyl, 3-fluoro-6-methylphenyl, 2-chloro-5-trifluoromethylphenyl, 2-chloro-4-methylphenyl, 3-chloro-4-methylthien-3-yl, 5,6,7,8-tetrahydronaphth-1-yl, and 4-chloro-5-methoxy-2-methylpyrimidin-4-yl; wherein $R^7$ is hydrogen or tetrahydropyran-2-yl; wherein X is thio or imino; and wherein n is 2.

A specifically preferred class of compounds of Formula IV consists of xylazine, flutonidine, moxonidine, tramazoline, tolonidine, piclonidine, tiamenidine, and clonidine.

Another class of compounds from which a suitable sympatholytic agent with sympathetic neurotransmitter depleting activity alone or in combination with alpha-2 adrenoreceptor agonist activity may be selected is represented by Formula V:

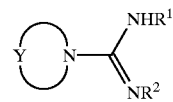

wherein Y represents the remainder of a cyclic structure selected from 1,2,3,4-tetrahydroisoquinoline or 2,3-dihydroisoindole, which may be substituted by one or more radicals selected from halogen, lower alkyl, alkoxy, hydroxyl, oxo, amino, dialkylamino, aryl, aryloxy, cyano, alkoxycarbonyl, aminocarbonyl, alkylsulfinyl, alkylsulfonyl, alkanoyl, or alkylthio; and wherein $R^1$ and $R^2$ are defined as in Formula II; or a pharmaceutically acceptable salt thereof.

An especially preferred class of compounds of Formula V consists of those compounds wherein Y is substituted tetrahydroisoquinoline, and wherein the preferred substituents are wither hydrogen or halogen, preferably on position 7 of the tetrahydroisoquinoline nucleus, and wherein $R^1$ and $R^2$ are both hydrogen.

A specifically preferred class of compounds of Formula V consists of debrisoquin and guanisoquin.

Another class of compounds from which a suitable sympatholytic agent with alpha-1 antagonist activity may be selected is represented in Formulas VI and VII:

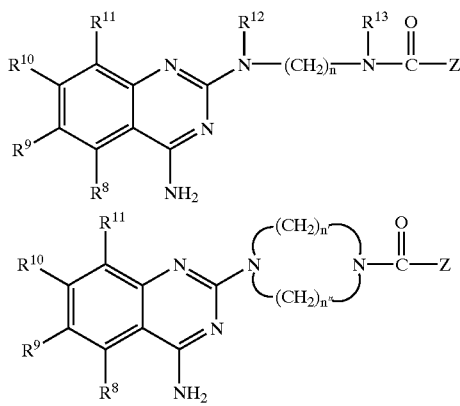

wherein $R^8$ is hydrogen, alkyl, or cycloalkyl; wherein $R^9$ and $R^{10}$ are independently selected from hydrogen, alkyl, alkoxy, acyloxy, dialkylamino, or alkylthio; wherein $R^{11}$ is selected from hydrogen, alkyl, or alkoxy; wherein $R^{12}$ and $R^{13}$ are independently selected from hydrogen or alkyl; wherein n' and n" independently represent values from 2 to 4 inclusive; and wherein Z may abe selected from alkyl, alkoxy, alkylaryl, alkenylaryl, alkoxyalkyl, hydroxyalkyl, aryl, heteroaryl, and heteroalkyl; or a pharmaceutically acceptable salt thereof.

A preferred class of compounds of Formula VI consists of those compounds wherein $R^8$ is hydrogen, $R^9$ and $R^{10}$ are both alkoxy; wherein $R^{11}$ is selected from hydrogen or alkoxy; and wherein $R^{12}$ is selected from hydrogen or alkyl.

A preferred class of compounds of Formula VII consists of those compounds wherein $R^8$ is hydrogen, $R^9$ and $R^{10}$ are both alkoxy; wherein $R^{11}$ is selected from hydrogen or alkoxy; and wherein n' and n" are independently either 2 or 3.

An especially preferred class of compounds of Formula VI consists of those wherein $R^9$ and $R^{10}$ are both methoxy; wherein an $R^{11}$ is selected from hydrogen or methoxy; wherein $R^{12}$ is selected from hydrogen or methyl; wherein $R^{13}$ is hydrogen; and wherein Z is selected from ethyl, propyl, butyl, 2-methylpropyl, 1-methoxyethyl, 2-(2-furoyl)-ethenyl, 2-tetrahydrofuranoyl, 2-furoyl, 2-hydroxy-2-methylpropyloxy, 2-hydroxypropyl, and 2-thiomethyl-1,3,4-oxadiozol-4-yl.

An especially preferred class of compounds of Formula VII consists of those compounds wherein $R^9$ and $R^{10}$ are both methoxy; wherein an $R^{11}$ is selected from hydrogen or methoxy; wherein Z is selected from ethyl, propyl, butyl, 2-methylpropyl, 1-methoxyethyl, 2-(2-furoyl)-ethenyl, 2-tetrahydrofuranoyl, 2-furoyl, 2-hydroxy-2-methylpropyloxy, 2-hydroxypropyl, and 2-thiomethyl-1,3,4-oxadiazol-4-yl; and wherein n' is 2 and n" is 2 or 3.

A specifically preferred class of compounds of Formulas VI and VII consists of alfuzosin, bunazosin, doxazosin, metazosin, neldazosin, prazosin, terazosin, trimazosin, tiodazosin, and MY-5561.

Another class of compounds from which a suitable sympatholytic agent with alpha-1 antagonist activity may be selected is represented in Formula VIII:

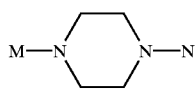

wherein N may be selected from aryl or heteroaryl, which may be substituted with one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, halogen, thioalkyl, dialkylamino, arylamino, alkylsulfinyl, alkylsulfonyl, arylsulfinyl or arylsulfonyl; and M can be further defined as:

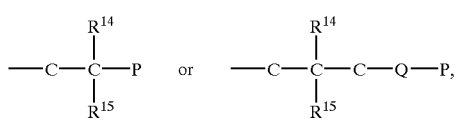

wherein $R^{14}$ and $R^{15}$ are independently selected from hydrogen, alkyl, alkoxy, or hydroxy; wherein P is selected from heteroaromatic or polycyclic heteroaromatic, which may be substituted by one or more radicals selected from halogen, alkyl, alkoxy, oxo, cyano, alkoxycarbonyl, arylalkyl, trifluromethyl, or aryloxyalkyl; and wherein Q is selected from oxygen or imino; or a pharmaceutically acceptable salt thereof.

A preferred class of compounds of Formula VIII consists of those compounds wherein N is phenyl, pyridyl, thienopyridinyl, indolyl, or pyrimidin-2-yl; wherein, if N is phenyl, then the phenyl ring may be substituted by one or more of the following preferred radicals: chloro, methoxy, cyano, thiomethyl, trifluoromethyl; wherein $R^{14}$ is hydroxy, ethoxy, or methoxy; wherein $R^{15}$ is hydrogen; and wherein P is selected from 3-pyridyl, 1-naphthyl, 2-quinazolin-1,3-dione, 6,7-methylenedioxyindol-2-yl, 1,3-pyrimidin-2,4-dion-6-yl; 3H-1,2,4-triazol-3-on-2-yl; 1,2,4-triazolo[4,3-a]pyridin-3(2H)-on-2-yl.

An especially preferred class of compounds of Formula VIII consists of those compounds wherein N is selected from phenyl, 3-chlorophenyl, 2-methoxyphenyl, 3-methoxyphenyl, 3-trifluoromethylphenyl, or 3-indolyl.

A specifically preferred class of compounds of Formula VIII consists of urapidil, solypertine, naftopidil, saterinone, trazodone, nefazodone, tiospirone, SGB-15343-[2-[4-(o-methoxyphenyl)-1-piperazinyl]ethyl]-2,4(1H,3H-quinazolinedione monohydrochloride, and IP-661-[2-ethoxy-2-(3'-pyridyl)ethyl]-4-(2'-methoxy-phenyl) piperazine.

Another class of compounds from which a suitable sympatholytic agent with alpha-1 adrenoreceptor antagonist activity may be selected is represented by Formula IX:

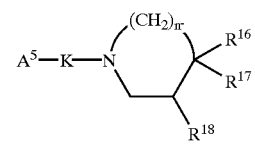

wherein $A^5$ is selected from aryl, aryloxy, arylalkyloxy, arylamino, cycloalkyl, cycloalkyloxy, arylcarbonyl, arylsulfonyl, heteroaryl, heteroarylcarbonyl, heteroaryloxy, heteroarylamino, and heteroarylsulfonyl, which may be substituted by one or more radicals selected from alkyl, branched alkyl, cycloalkyl, hydroxyl, alkoxy, cycloalkylalkyl, alkoxyalkyl, aryl, alkanoyl, alkoxycarbonyl, carboxyl, amino, cyano, oxo, halogen, thioalkyl, dialkylamino, heterocyclic, arylamino, alkylsulfinyl, alkylsulfonyl, arylsulfinyl, or arylsulfonyl; wherein K is selected from linear alkylene of 0 to 6 methylene units in length, branched alkylene, alkenyl, cycloalkyl, or arylalkyl; wherein $R^{16}$ and $R^{17}$ may be independently selected from hydrogen, alkyl, aryl, arylalkyl, heteroaryl, arylcarbonyl, arylamino, arylcarbonylamino, arylsulfonylamino, carboxylate, aryloxycarbonyl, or heteroarylcarbonyl; or wherein $R^{16}$ and $R^{17}$ together represent a double bond linked to an adjacent substituted carbon; or wherein $R^{16}$ and $R^{17}$ represent a spirocyclic ring juncture forming an alicyclic or heterocyclic ring; wherein $R^{18}$ may be selected from hydrogen, alkyl, alkoxy, aryl, aryloxy, arylamino, or arylcarbonylamino; and wherein N'" represents a value of 1 to 3; or a pharmaceutically acceptable salt thereof.

A preferred class of compounds of Formula IX consists of those compounds wherein $A^5$ is selected from substituted phenyl, heteroaromatic, or heterocyclic structures; wherein K is a linear alkylene chain of 1 to 4 methylene units in length; wherein R16 is selected from hydrogen, phenyl, substituted phenyl, heteroaromatic, arylcarbonyl, or arylcarbonylamino; wherein $R^{17}$ is selected from hydrogen or methyl; or wherein $R^{16}$ and $R^{17}$ together represent a double bond attached to a substituted carbon, preferably a diaryl substituted carbon; wherein $R^{16}$ and $R^{17}$ taken together represent attachment points for a spirocyclic ring moiety, preferably selected from 1,3-dioxalane, or 5,5'-oxazolidin-3-one; and wherein R18 may be selected from hydrogen or arylcarbonylamino.

A specifically preferred class of compounds of Formula IX consists of piperoxan, proroxan, fenspiride, indoramin, and lidanserin.

Another class of compounds from which a suitable sympatholytic agent with alpha-1 adrenoreceptor antagonist activity is represented by Formula X:

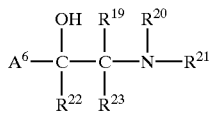

wherein $A^6$ may be selected from aryl, aryloxy, heteroaryl, heteroaryloxy, arylthio, heteroarylthio, arylalkyl, and heteroarylalkyl, which may be substituted by one or more radicals selected from chloro, hydroxyl, alkoxy, alkyl, amino, aminoalkyl, arylsulfonamino, alkylsulfonamino, aminocarbonyl, aminosulfonyl, thiol, aryl, heteroaryl, or alkylthio; wherein $R^{19}$, $R^{22}$, and $R^{23}$ may be independently selected from hydrogen or alkyl; wherein $R^{20}$ may be selected from hydrogen or alkyl; wherein R21 may be further described as:

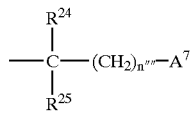

wherein $R^{24}$ and $R^{25}$ may be independently selected from hydrogen or alkyl; wherein $A^7$ is aryl, preferably phenyl or substituted phenyl; and n"" represents a value of 0 to 4 methylene units. Additionally, Formula X describes compounds wherein $R^{20}$ and $R^{21}$ taken together represent contact points which form a ring, such as pyrrolidine or piperidine, which may be further substituted; or a pharmaceutically acceptable salt thereof.

A preferred class of compounds of Formula X consists of those compounds wherein $A^6$ is selected from phenyl, substituted phenyl, carbostyril, 2,3-dihydrobenzo[b]thiophen-5-yl, and thiazolyl-2-thio; wherein $R^{19}$ is hydrogen; wherein $R^{23}$ is hydrogen or methyl; wherein R20 is hydrogen; wherein $R^{24}$ and $R^{25}$ are independently hydrogen or methyl; and wherein $A^7$ is phenyl.

Another preferred class of compounds of Formula X consists of those compounds wherein $R^{20}$ and $R^{21}$ together form a piperidine moiety, which is further substituted by a phenylmethyl substituent.

A specifically preferred class of compounds of Formula X consists of labetalol, amosulalol, arotinolol, brefanolol, ifenprodil and tibalosin.

Another class of compounds from which a suitable sympatholytic agent may be selected as an irreversible alpha-1 adrenoreceptor antagonist is represented by Formula XI:

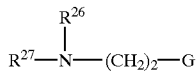

wherein $R^{26}$ and $R^{27}$ are independently selected from alkyl, arylalkyl, aryloxyalkyl, or heteroalkyl; or wherein $R^{26}$ and $R^{27}$ taken together represent a ring structure; and wherein G represents a suitable leaving group substituent selected from halogen, alkylsulfonyloxy, or arylsulfonyloxy; or a pharmaceutically acceptable salt thereof.

A preferred class of compounds of Formula XI consists of those compounds wherein $R^{26}$ and $R^{27}$ are independently taken from phenylalkyl or phenyloxyalkyl, and G is chloro.

A specifically preferred class of compounds of Formula XI consists of phenoxybenzamine and dibenzamine.

Another class of compounds from which a suitable sympatholytic agent may be selected as an alpha-2 adrenoreceptor agonist is represented by Formula XII:

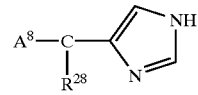

wherein $A^8$ is selected from aryl or heteroaryl, which may be substituted by one or more radicals independently selected from alkyl, halogen, alkoxy, alkylthio, hydroxyl, amino, arylsulfonylamino, of carboxamido; and wherein $R^{28}$ is selected from hydrogen or alkyl; or a pharmaceutically acceptable salt thereof.

A preferred class of compounds of Formula XII consists of those compounds wherein $A^8$ is phenyl or substituted phenyl, and $R^{28}$ is hydrogen or methyl.

A specifically preferred class of compounds of Formula XII consists of detomidine and medetomidine.

A suitable sympatholytic agent with alpha-1 adrenoreceptor antagonist activity or sympathetic neurotransmitter depleting activity may also be selected from the structural class of compounds known generically as the Rauwolfia alkaloids. As described in *Burger's Medicinal Chemistry*, *4th Edition*, Part III, pages 302–305 and 932–933 (M. E. Wolff, editor, Wiley-Interscience, New York, 1981), compounds in this class are well known sympatholytic agents. Specifically preferred compounds of this class are reserpine, mediodespidine, deserpidine, rauwulscine, and extracts of *Rauwolfia serpentina*; or a pharmaceutically acceptable salt thereof.

A suitable sympatholytic agent with alpha-1 adrenoreceptor antagonist activity may also be selected from the class of compounds known generally as the ergot alkaloids. As described in *Burger's Medicinal Chemistry*, *4th Edition*, Part III, page 310 (M. E. Wolff, editor, Wiley-Interscience, New York; 1981), compounds of this class are well known sympatholytic agents. Specifically preferred compounds from this class are nicergoline, dihydroergocornine, dihydroergocryptine, dihydroergocristine, amsulosin, BAM-1125, and the mixture of hydrogenated derivatives of the ergotoxine alkaloids.

Another class of compounds from which a suitable sympatholytic agent may be selected as an inhibitor of dopamine beta-hydroxylase is represented by Formula XIII:

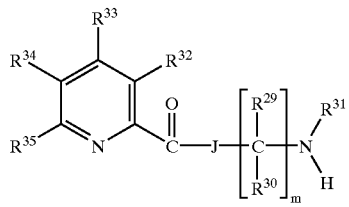

wherein each of $R^{32}$ through $R^{35}$ is independently selected from hydrido, alkyl, haloalkyl, mercapto, alkylthio, cyano, alkoxy, alkoxyalkyl and cycloalkyl; wherein J is selected from oxygen atom and sulfur atom; wherein each of $R^{29}$ and $R^{30}$ is independently selected from hydrido and alkyl; wherein $R^{31}$ is selected from hydrido, alkyl, cycloalkyl, hydroxyalkyl, haloalkyl, cycloalkylalkyl, alkoxyalkyl, arylalkyl, aryl, alkanoyl, alkoxycarbonyl, carboxyl,a amino, cyanoamino, monoalkylamino, dialkylamino, alkylsulfinyl, Another preferred class of compounds within Formula XIII consists of those compounds of Formula XIV:

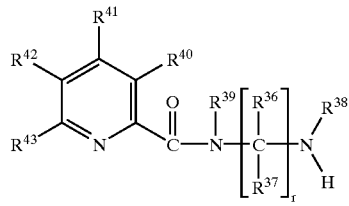

wherein each of $R^{36}$, $R^{37}$ and $R^{40}$ through $R^{43}$ is independently selected from hydrido, hydroxy, alkyl, cycloalkyl, cycloalkylalkyl, arylalkyl, aryl, alkoxy, arylalkoxy, aryloxy, alkoxyalkyl, haloalkyl, hydroxyalkyl, halo, cyano, amino, monoalkylamino, dialkylamino, carboxy, carboxyalkyl, alkanoyl, alkenyl, cycloalkenyl and alkynyl; wherein $R^{36}$ and $R^{37}$ together may form oxo or thio; wherein r is a number selected from zero through six, inclusive; wherein each of $R^{38}$ and $R^{39}$ is independently selected from hydrido, alkyl, cycloalkyl, hydroxyalkyl, haloalkyl, cycloalkylalkyl, alkoxyalkyl, aralkyl, aryl, alkanoyl, alkoxycarbonyl, carboxyl, amino, cyanoamino, monoalkylamino, dialkylamino, alkylsulfinyl, alkylsulfonyl, arylsulfinyl and arylsulfonyl.

A more preferred class of compounds within Formula XIV consists of those compounds wherein each of $R^{36}$, $R^{37}$ and $R^{40}$ through $R^{43}$ is independently selected from hydrido, hydroxy, alkyl, phenalkyl, phenyl, alkoxy, benzyloxy, phenoxy, alkoxyalkyl, hydroxyalkyl, halo, amino, monoalkylamino, dialkylamino, carboxy, carboxyalkyl and alkanoyl; wherein r is a number selected from zero through four, inclusive; wherein each of $R^{38}$ and $R^{39}$ is independently selected from hydrido, alkyl, amino, monoalkylamino, dialkylamino, phenyl and phenalkyl.

An even more preferred class of compounds within Formula XIV consists of those compounds where in each of $R^{36}$, $R^{37}$ and $R^{40}$ is independently selected from hydrido, hydroxy, alkyl, alkoxy, amino, monoalkylamino, carboxy, carboxyalkyl and alkanoyl; wherein r is a number selected from zero through three, inclusive; and wherein each of $R^{38}$ and $R^{39}$ is selected from hydrido, alkyl, amino and monoalkylamino. Most preferred are compounds wherein each of $R^{40}$ through $R^{43}$ is independently selected from hydrido and alkyl; wherein each of $R^{36}$ and $R^{37}$ is hydrido; wherein r is selected from zero, one and two; wherein $R^{38}$ is selected from hydrido, alkyl and amino; and wherein $R^{39}$ is selected from hydrido and alkyl. Especially preferred within this class is the compound 5-n-butylpicolinic acid hydrazide (fusaric acid hydrazide).

Another class of compounds from which a suitable sympatholytic agent with dopamine beta-hydroxylase inhibitor activity may be selected to provide the conjugate first residue is represented by Formula XV:

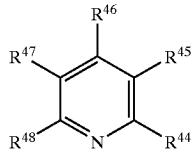

wherein each of $R^{44}$ through $R^{48}$ is independently selected from hydrido, hydroxy, alkyl, cycloalkyl, cycloalkylalkyl, aralkyl, aryl, aryloxy, alkoxy, alkylthio, aralkoxy, alkoxyalkyl, haloalkyl, hydroxyalkyl, halo, cyano, amino, monoalkylamino, dialkylamino, amido, alkylamido, hydroxyamino, carboxyl, carboxyalkyl, alkanoyl, alkenyl, cycloalkenyl, alkynyl, cyanoamino, carboxyl, tetrazolyl, thiocarbamoyl, aminomethyl, alkylsulfanamido, nitro, alkylsulfonyloxy, formoyl and alkoxycarbonyl; with the proviso that at least one of $R^{44}$ through $R^{48}$ is

wherein A' is —Co—$R^{49}$ or —$NR^{51}R^{52}$ wherein $R^{49}$ is selected from hydrido, alkyl, hydroxy, alkoxy, alkylthio, phenyl, phenoxy, benzyl, benzyloxy, —$OR^{50}$ and —$NR^{53}R^{54}$, wherein $R^{50}$ is selected from hydrido, alkyl, cycloalkyl, cycloalkylalkyl, phenyl and benzyl; wherein each of $R^{51}$ through $R^{54}$ is independently selected from hydrido, alkyl, cycloalkyl, hydroxyalkyl, haloalkyl, cycloalkylalkyl, alkoxyalkyl, aralkyl, aryl, alkanoyl, alkoxycarbonyl, carboxyl, amino, cyanoamino, monoalkylamino, dialkylamino, alkylsulfinyl, alkylsulfonyl, arylsulfinyl and arylsulfonyl; wherein t is a number selected from zero through four, inclusive; or a pharmaceutically-acceptable salt thereof.

A preferred family of compounds within Formula XV consists of those compounds characterized as chelating-type inhibitors of Formula XVI:

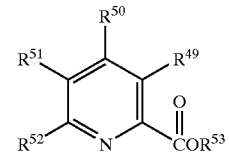

wherein each of $R^{49}$ through R52 is independently selected from hydrido, hydroxy, alkyl, cycloalkyl, phenyl, benzyl, alkoxy, phenoxy, benzyloxy, alkoxyalkyl, hydroxyalkyl, halo, cyano, amino, monoalkylamino, dialkylamino, amido, alkylamido, hydroxyamino, carboxyl, carboxyalkyl, alkanoyl, cyanoamino, carboxyl, thiocarbamoyl, aminomethyl, nitro, formoyl, formyl and alkoxycarbonyl; and wherein $R^{53}$ is selected from hydrido, alkyl, phenyl and benzyl.

A class of specifically-preferred compounds of Formula XVI consists of:

5-n-butylpicolinic acid (fusaric acid);
5-n-butylpicolinic acid (fusaric acid);
picolinic acid;
5-nitropicolinic acid;
5-aminopicolinic acid;
5-N-acetylaminopicolinic acid;
5-N-propionylaminopicolinic acid;
5-N-hydroxyaminopicolinic acid;
5-iodopicolinic acid;
5-bromopicolinic acid;
5-chloropicolinic acid;
5-hydroxypicolinic acid;
5-methoxypicolinic acid;
5-N-propoxypicolinic acid;
5-N-butoxypicolinic acid;
5-cyanopicolinic acid;
5-carboxylpicolinic acid;
5-n-butyl-4-nitropicolinic acid;
5-n-butyl-4-methoxypicolinic acid;

5-n-butyl-4-ethoxypicolinic acid;
5-n-butyl-4-aminopicolinic acid;
5-n-butyl-4-hydroxyaminopicolinic acid; and
5-n-butyl-4-methylpicolinic acid.

Especially preferred of the foregoing class of compounds of Formula XVI is the compound 5-n-butylpicolinic acid (fusaric acid).

Another class of compounds from which a suitable sympatholytic agent with dopamine beta-hydroxylase inhibiting activity is represented by Formula XVII:

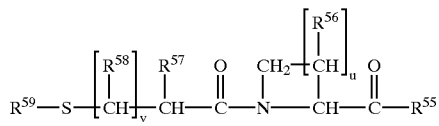

wherein $R^{55}$ is hydrido, hydroxy, alkyl, amino and alkoxy; wherein $R^{56}$ is selected from hydrido, hydroxy and alkyl; wherein each of $R^{57}$ and $R^{59}$ is independently selected from hydrido, alkyl and phenalkyl; wherein $R^{59}$ is selected from hydrido and $R^{60}C-$ with $R^{60}$ selected from alkyl, phenyl and phenalkyl; wherein u is a number from one to three, inclusive; and wherein v is a number from zero to two, inclusive; or a pharmaceutically-acceptable salt thereof.

A preferred class of compounds within Formula XVII consists of those compounds wherein $R^{55}$ is selected from hydroxy and lower alkoxy; wherein $R^{56}$ is hydrido; wherein $R^{57}$ is selected from hydrido and lower alkyl; wherein $R^{58}$ is hydrido; wherein $R^{59}$ is selected from hydrido and $R^{60}C-$ with $R^{60}$ selected from lower alkyl and phenyl; wherein u is two; and wherein v is a number from zero to two, inclusive.

A more preferred class of compounds within Formula XVII consists of those compounds of Formula XVIII

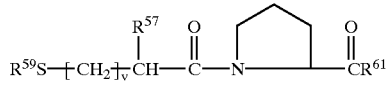

wherein $R^{61}$ is selected from hydroxy and lower alkyl; wherein $R^{57}$ is selected from hydrido and lower alkyl; wherein $R^{59}$ is selected from hydrido and $R^{60}C-$ with $R^{60}$ selected from lower alkyl and phenyl and v is a number from zero to two, inclusive.

A more preferred class of compounds within Formula XVIII consists of those compounds wherein $R^{61}$ is hydroxy; wherein $R^{57}$ is hydrido or methyl; wherein $R^{59}$ is hydrido or acetyl; and wherein n is a number from zero to two, inclusive.

Most preferred within the class of compounds of Formula XVIII are the compounds 1-(3-mercapto-2-methyl-1-oxopropyl)-L-proline and 1-(2-mercaptacetyl)-L-proline (also known as captopril.)

Specifically preferred sympatholytic compounds which are not encompassed in Formulas I through XVIII from which a suitable agent may be selected include the sympathetic neurotransmitter depleting agents bretylium and MJ-10459, and the alpha-1 adrenergic antagonist methylapogalanthamine.

α-Adrenergic blocking agents bind selectively to the a class of adrenergic receptors and thereby interfere with the capacity of sympathomimetic amines to initiate actions at these sites. α-Adrenergic blockade is due to the direct action of these drugs on a receptors and is independent of any effects on adrenergic neurons or on the basic response mechanisms of effector cells. β-Adrenergic receptors are not affected by conventional doses of any α-blocking agent currently in use.

Examples of α-adrenergic antagonists include phenoxybenzamine, dibenzamine, phentolamine, tolazoline, and prazosin. Phenoxybenzamine and dibenzamine bind covalently to the a receptor and produce an irreversible type of blockade. Phentolamine, tolazoline, and prazosin bind reversibly and antagonize the actions of sympathomimetic amines competitively. There are differences in the relative abilities of α-adrenergic blocking agents to antagonize the effects of sympathomimetic amines at the two subtypes of a receptors, $\alpha_1$ and $\alpha_2$ receptors. Phenoxybenzamine is approximately 100-fold more potent in blocking $\alpha_1$ (postsynaptic) receptors than $\alpha_2$ receptors (that modulate neural release of transmitter). Prazosin is also a highly selective $\alpha_1$-blocking agent, while phentolamine is only three to five times more potent in inhibiting $\alpha_1$-than $\alpha_2$-adrenergic receptors. In contrast, yohimbine is a selective $\alpha_2$ blocker and has been shown to prevent the antihypertensive effect of systemic clonidine. Phentolamine is the preferred α-adrenergic antagonist at this time.

These compounds have previously been administered systemically, either orally or by injection. Systemic administration requires high doses and thus systemic side effects (e.g., postural hypotension, tachycardia, nasal stuffiness, headache) limit their usefulness. In the method described herein, the compounds are administered topically, in a suitable pharmaceutical carrier, many of which are known to those skilled in the art. The carrier can be in the form of a lotion, ointment, solution, or transdermal patch. Topical administration also includes iontophoresis wherein an electric current drives the drug, in the form of an ion such as a pharmaceutically acceptable salt, into the skin. The topical application allows the drug to reach high concentration at the desired target without appreciable systemic dosing. Thus the many of the side effects of these compounds, observed following systemic administration, are avoided by topical administration.

Another drug class, $\alpha_2$-agonists, the preferred example being clonidine, an antihypertensive agent stimulating both central and peripheral $\alpha_1$- and $\alpha_2$-adrenergic receptors, also antagonize the effects of norepinephrine. This is because sympathetic terminals possess $\alpha_2$-receptors which when activated block the release of norepinephrine. Thus the $\alpha_2$-agonists such as clonidine antagonize $\alpha_1$-receptors indirectly by preventing the release of norepinephrine.

A third class of effective drugs are those that deplete norepinephrine from the sympathetic terminals. The prototype drug in this class is guanethidine. Other examples are bretyliut, bethanidine, debrisoquin, and reserpine.

Additional compounds are specific inhibitors of catecholamine synthesis and monoamine oxidase inhibitors.

These compounds are normally administered systemically (orally or by intravenous injection), although as described herein they are administered in a pharmaceutically acceptable topical carrier or by iontophoresis, as described above.

The effective dosage of these compounds is determined by applying dosages of the compound to the affected site and observing local vasodilatation. Vasodilatation can be determined by laser Doppler flow measurements or by measuring local increases in skin temperature.

EXAMPLE 1

Demonstration of Effectiveness of Intravenous Administration of Blocking Agent

If peripheral α-adrenergic receptors are blocked completely, skin temperature would approach core temperature. Such a blockage would produce profound hypotension and a reflex tachycardia. Therefore, a cumulative dose of phentolamine was selected such that the heart rate did not exceed 150 beats per minute and the effects on blood pressure were mild. This dose ranged from 35 mg to 45 mg over a 30 minute period. Preliminary studies suggested that this amount of phentolamine effectively relieved pain in patients with SMP.

The heart rate, systolic and diastolic blood pressure changes produced by phentolamine in a typical patient were relatively mild. In the first seven patients phentolamine alone was administered. The heart rate increased moderately. In subsequent sessions, patients pretreated with propranolol 1–2 mg showed minimal increase in pulse rate. Blood pressure was little effected regardless of whether propranolol was given as patients were maintained in a supine position.

One patient, an 18 year old woman, was treated for severe pain in the right foot. The patient had a thorough examination but no clear initiating cause of the pain was determined. The patient was disabled and could not walk due to the severity of the pain. A thorough neurological exam disclosed a restricted zone of hyperalgesia on the plantar surface of the foot that was consistent over several examinations. No psychiatric problems were present in an otherwise normal productive college student performing well in school.

The patient was diagnosed as having SMP and then underwent local LABSG, and the administration of phentolamine systemically by intravenous injection.

Placebo trials indicated that patient showed no change in pain when normal saline was injected IV.

Phentolamine given IV with an accumulated dose of 25 mg over 15 minutes led to an 80% reduction in pain as measured by visual analysis scores and LABSG led to 50% relief of pain in a separate study.

Ratings of stimulus-independent pain did not change for 10 minutes following the initial phentolamine administration. The first 4 boli of phentolamine (total dose=15 mg) resulted in a gradual decrease in pain of about 50%. After two further injections each of 10 mg, over 80% of the patient's pain was relieved. The slow time course of pain relief suggests that the total cumulative dose is the relevant dose parameter.

Five minutes after the last phentolamine dose, 0.5 mg propranolol was given intravenously to counteract the tachycardia that was starting to become uncomfortable to the patient. This did not add appreciably to the analgesia already achieved with the α-adrenergic blockade. Propranolol was shown not to affect pain in patients. The patient's pain remained at this low level for about two hours, despite a plasma half-life of approximately 20 minutes for phentolamine. Pain gradually returned over the course of about three hours.

The LABSG procedure failed to afford long-term relief and the patient subsequently underwent a surgical lumbar sympathectomy. The patient had complete pain relief from this procedure and continues to be pain free as of 15 months post operatively.

Seventeen patients received both phentolamine and LABSG. The time of maximum relief of stimulus evoked pain correlated highly with the time at which there was maximum relief of stimulus-independent pain. All pain scores were converted to percent pain relief. The peak relief of stimulus independent pain for the LABSG compares favorably to the peak relief obtained from the phentolamine block. The range of peak relief for both procedures extended from near zero to 100%. Patients with less than 50% pain relief from both procedures were considered to have pain independent of SMP. There was a high correlation of the results of the two procedures (r=0.78). This shows that patients who experience substantive pain relief from LABSG also obtain substantive pain relief from phentolamine.

In five patients in whom the phentolamine block afforded more than 50% pain relief, the duration of pain relief lasted for several hours. The pain returned to within 75% of baseline within 2 to 7 hours.

Only one patient reported 45% maximum relief of pain with the LABSG but no relief with the phentolamine block.

There was a suggestion of greater specificity of results with phentolamine compared to LABSG. Of those patients who had 50% or greater pain relief following LABSG, the mean pain relief with phentolamine was 75% vs. 60% for the LABSG.

Side effects associated with the phentolamine administration other than the hemodynamic changes discussed above were minimal. The principal side effects observed were nasal stuffiness (12 patients), headache (3 patients), and dizziness (2 patients). The complications of the LABSG included mild headache, mild dizziness, back and neck pain from the needles, temporary paresis, and concurrent somatic block (thus negating LABSG) and requiring another procedure. When patients were asked which of the two sympathetic blocks they preferred, the patients chose the phentolamine block.

EXAMPLE 2

Topical Administration of Clonidine for Relief of SMP

A patient with a sciatic nerve injury was diagnosed as having SMP, based on lumbar sympathetic blockage. The patient had ongoing pain and intense hyperalgesia to both mechanical and cold stimuli in the painful zone. Clonidine was applied to the hyperalgesic zone transdermally via a 7.0 or 10.5 cm$^2$ patch (Catapres-TTS; Boehringer). These patches deliver 0.2 mg or 0.3 mg of clonidine/day for 7 days. A series of 6 patches were applied consecutively to different sites and each left in place for 2–10 days. Prior to, during, and post drug application, the heart rate and blood pressure were taken and sensory testing performed. Pain evoked by mechanical and cold stimuli was rated on a scale from 0–10.

Complete relief of hyperalgesia in the skin underlying the patch was achieved from each clonidine patch. There were no adverse side effects or changes in cardiovascular parameters. The skin surrounding the patch remained hyperalgesic even in the region adjacent to the edge of the patch. At each patch-site, the pain evoked by deep pressure, light brushing and cooling stimuli was reduced within 24–36 hours and was completely abolished within 48 hours following patch application. This effect persisted for more than 24 hours after removal of the patch. A local anesthetic effect is unlikely since the patch did not alter (1) the detection threshold to mechanical stimuli in the patient, or (2) the detection or the pain threshold to mechanical stimuli in a normal subject.

EXAMPLE 3

Topical Administration of Clonidine Compared with Topical Administration of Clonidine followed by Intradermal Injections of α-Adrenergic Agonists Methods Patient Selection and Control Subjects: Six normotensive patients with chronic ongoing pain and cutaneous hyperalgesia to mechanical and cooling stimuli following soft tissue or nerve trauma were examined. All patients had previously undergone sympathetic blocks (i.e., local anesthetic blockade of the appropriate sympathetic ganglia) to assess the involvement of the sympathetic nerves in their pain state. Additionally, in all but one patient (case 2) a systemic α-adrenergic block was performed via intravenous administration of phentolamine. Four of the six patients (cases 1–4) experienced 70–100% pain relief following the blocks and were considered to have SMP. The remaining two patients. (cases 5, 6) were considered to have sympathetically-independent pain (SIP) since their pain was not affected by local anesthetic sympathetic ganglion block or the phentolamine block.

Five normal subjects were used as controls. One subject was used to investigate the effect of clonidine on normal skin (i.e., the top of the foot). The four remaining subjects were used to assess the effect of intradermal norepinephrine and phenylephrine in normal skin.

Topical Clonidine: Clonidine was administered to the hyperalgesic skin via a 7.0 or 10.5 cm$^2$ patch (Catapres-TTS$^R$-2 and TTS$^R$-3, Boehringer Ingelheim). These patches deliver a systemic does of 0.2 mg and 0.3 mg respectively of clonidine/day (i.e., 30 µg/cm$^2$/day) for a maximum of 7 days. A series of 2–7 patches were applied consecutively to different sites within the hyperalgesic zone. Each patch was left in place for 2–10 days within this affected zone. Prior to, during and immediately after drug application, the following parameters were monitored: heart rate, blood pressure, ongoing pain and pain to mechanical and cold stimuli.

Sensory Testing: To assess the local and systemic effects of clonidine, the following measures were used before application of the patch and immediately after removal of the patch: 1) Ongoing pain: stimulus-independent pain was assessed on a visual analog scale (VAS). The scale consisted of a 100 mm line where "no pain" and "most intense pain" were indicated on the left and right ends of the scale respectively. 2) Hyperalgesia to mechanical and cooling stimuli: Pain evoked by mechanical and cold stimuli was rated verbally on a scale from 0 ("no pain") to 10 ("most intense pain"). The mechanical stimuli included innocuous brushing with a camel's hair brush and innocuous pressure from the 206 g weight of a 13 mm diameter (i.e., 2N) brass probe. Pain thresholds to mechanical stimuli were determined in the area within and surrounding the patch sites using calibrated von Frey filaments. The cooling stimulus consisted of small drops of acetone lightly placed onto the patient's skin. Patients with SMP typically find that the 1–2° C. decrease in temperature induced by such a stimulus is painful. 3) Tactile sensibility: To rule out local anesthetic effects, the detection (touch) thresholds were determined in the area within the surrounding selected patch sites using calibrated von Frey filaments. In addition, the patient's ability to distinguish the blunt from the sharp ends of a pin was also assessed. The patients were instructed to close their eyes during the hyperalgesia and von Frey threshold testing procedures.

Effects of Intradermal Norepinephrine and Phenylephrine: In two patients, intradermal injections of the non-specific α-adrenergic agonist norepinephrine (5 µg in 10 µl normal saline) or the α-adrenergic agonist phenylephrine (10 µg in 10 µl normal saline) were made at a patch site immediately after removing the patch. Norepinephrine and phenylephrine injections were also made at control sites on the patients' normal limb and into the normal skin of 4 healthy control subjects. Similar injection sites were chosen for the control subjects and patients. All injection were made in a single-blinded fashion. The patients and control subjects were instructed to rate the magnitude of any evoked pain and resultant hyperalgesia on a verbal scale from 0 to 10.

Results

The results of the clonidine applications in the control subject and six patient cases are summarized in Table 1. The first patient was studied extensively and is presented in detail as an illustrative example.

TABLE I

Summary of Individual Case Results

| Case Number | | | | | |
|---|---|---|---|---|---|
| 1 | 2 | 3 | 4 | 5 | 6 |
| SMP | SMP | SMP | SMP | SIP | SIP |

Age/Sex:

| | | | | | |
|---|---|---|---|---|---|
| 30/F | 45/F | 35/M | 52/F | 52/M | 42/F |

Duration of Symptoms (Years):

| | | | | | |
|---|---|---|---|---|---|
| 3 | 1.5 | 18 | 2 | 7 | 0.5 |

Extremity Affected:

| | | | | | |
|---|---|---|---|---|---|
| lower | lower | lower | face | upper | lower |

Mechanical Hyperalgesia:

pre-clonidine

| | | | | | |
|---|---|---|---|---|---|
| + | + | + | + | + | + | post-clonidine

| | | | | | |
|---|---|---|---|---|---|
| − | − | nt | − | + | + |

Touch Detection Threshold:

pre-clonidine (bars)

| | | | | | |
|---|---|---|---|---|---|
| 4 | 1 | 1.5 | 0.5 | 1 | 2 | post-clonidine (bars)

| | | | | | |
|---|---|---|---|---|---|
| 4 | 1 | 1.5 | 0.5 | 1 | 2 |

SMP = sympathetically maintained pain
SIP = sympathetically independent pain
+ = present, − = absent; nt = not tested Case 1:

The patient was a 30 year old, normotensive, white female who sustained an injury to the sciatic nerve from hip replacement surgery three years prior to entering the study. Subsequently, the patient developed continuous pain and hyperalgesia in the antero-lateral aspect of her left leg from the knee to the foot. Thermography revealed that most of this area was 1–2° C. colder than corresponding parts of the contralateral leg. Within the affected region, the patient experienced intense ongoing pain and was exquisitely sensitive to mechanical stimuli. Mild mechanical stimuli (e.g., light brushing or pressure) evoked severe pain. Cooling stimuli (e.g., acetone) were not detected when applied to some parts of the affected area and were painful when applied to other parts. The results of local anesthetic sympathetic ganglion blocks and i.v. phentolamine blocks confirmed that her ongoing pain and hyperalgesia were sympathetically maintained.

This patient received a series of 7 clonidine patches. The patch was applied for 36 hours to an area of skin which had previously been hyperalgesic to brushing, pressure and cooling stimuli. After removal of the patch, mechanical (brush, pressure) and cooling (a drop of acetone) stimuli applied to this region were detected but were not painful, although these stimuli still elicited pain when applied to the adjacent skin. The mechanical detection thresholds inside and outside the patch site were identical and were similar to the contralateral leg. Within the patch site, the pain threshold to von Frey filaments approximated the patient's 'normal' pain threshold at a corresponding contralateral site and far exceeded the mechanical detection threshold. The ability to distinguish sharp from blunt stimuli were not affected at this site after the patch was removed. Outside the patch site, the pain threshold was low and approached the detection threshold. The patient's ratings of her stimulus-independent pain were not affected by the patch.

Although the patient was pleased with the relief achieved from the patches, treatment was discontinued when the patches started to produce skin irritations. Six months following the termination of the clonidine trial, she underwent a lumbar sympathectomy that completely eliminated her pain and hyperalgesia.

Extent of Pain and Hyperalgesia Relief By Topical Clonidine:

A summary of the effect of four of the clonidine patches in which quantitative sensory testing was performed for case #1 is shown in FIG. 2. Each clonidine patch-greatly reduced and, in many cases, completely eliminated the patient's hyperalgesia to mechanical stimuli. A confounding local anesthetic effect did not occur since detection thresholds were unchanged. The time course of the effect of each patch was not evaluated quantitatively. However, the patient did note a reduction of her mechanical hyperalgesia within 36–48 hours after the patch was applied to the skin. After removing a patch, hyperalgesia was still absent for at least 12 hours. Typically, the patient's hyperalgesia returned within less than a week of the patch application.

The three remaining patients diagnosed as having SMP achieved relief of their hyperalgesia following topical application of clonidine without any accompanying change in touch detection threshold (see Table I; cases 2–4). The original zone of hyperalgesia in two of these patients (cases 2,3) encompassed greater than half of the lower extremity. For these patients, topical clonidine only eliminated hyperalgesia at or near the site of drug application and did not alter stimulus-evoked pain outside these sites. Furthermore, these patients did not report any reduction in their overall level of stimulus-independent pain. In case #4, the zone of pain and hyperalgesia radiated laterally from a small region above the vermillion border in the maxillary nerve distribution. Following clonidine application to the upper lip, complete relief of hyperalgesia was obtained throughout the entire affected zone. The patient's ongoing pain was reduced by 50–75% and was confined to a very small region above the lip.

One of the patients diagnosed as having SIP (see Table I; case 5) had pain and hyperalgesia in the median nerve distribution of the left hand. Neither the patient's hyperalgesia nor ongoing pain were improved by application of clonidine to the palmar aspect of the hand. The second patient diagnosed as having SIP (case 6) had pain and hyperalgesia in the foot. The clonidine patches were applied to the dorsum of the foot and resulted in only a slight reduction (by approximately 35%) in both ongoing pain and in the mechanical hyperalgesia to brush stimuli. The hyperalgesia to cold stimuli was not affected by the clonidine patches.

Side Effects:

The side effects from these clonidine patches were minor. The patients occasionally complained of feeling sleepy, thirsty and/or of having dry eyes. Following some of the patch applications, an erythematous rash was observed surrounding the patch site. This became a problem in two patients (cases 1, 4) and further treatment had to be discontinued despite good hyperalgesia relief. No appreciable alteration in the blood pressure or heart rate was apparent in any of the patients.

Sensory Effects of Topical Clonidine in Normal Skin:

To exclude further local anesthetic effects of clonidine, a clonidine patch was applied to the top of a normal subject's foot and sensory testing was performed prior to and 40 hours after the patch application. Neither the pain nor detection threshold to von Frey filaments were affected in this subject. Mechanical and cooling stimuli were detected but were not painful before or after the clonidine had been applied.

Effect of Norevinephrine and Phenylephrine:

To test the hypothesis that clonidine acts peripherally via reduction of norepinephrine release, an intradermal injection of norepinephrine (5 $\mu$g in 10 $\mu$l saline) was made at a previously hyperalgesic site that had been treated effectively with clonidine (case 1). Following removal of the clonidine patch and just prior to the injection, lightly brushing the skin at this site was only mildly hyperalgesic (rated 1 out of 10) whereas brushing the untreated skin evoked a pain sensation rated as 4 out of 10. The norepinephrine injection evoked an intense, burning pain sensation that subsided after four minutes. Twenty-five minutes after the injection, the patient's mechanical hyperalgesia at the patch site was rekindled and was rated as 3.5 out of 10. Injection of norepinephrine into the normal limb of this patient and the normal limb of another SMP patient (case 4), also evoked intense pain, but did not result in hyperalgesia. In contrast, intradermal injection of norepinephrine into the leg of four control subjects evoked a mild, short lasting pain and no hyperalgesia. Since topical application of an $\alpha_2$-adrenergic agonist relieved hyperalgesia and a non-specific agonist rekindled hyperalgesia, it was hypothesized that $\alpha_1$-adrenergic receptors play an important role in SMP. To test this hypothesis directly the specific $\alpha_1$-adrenergic agonist phenylephrine was injected intradermally (10 $\mu$g in 10 $\mu$l saline) at a clonidine patch site and a normal site (volar forearm) in a patient with SMP (case #4) following 3 days of clonidine treatment. This patient's pain and hyperalgesia, which was localized to a small region of the face, was relieved by clonidine. Injection of phenylephrine at the clonidine patch site evoked intense stinging pain that subsided approximately 3 minutes after the injection. Approximately 25 minutes after the injection, the patient's hyperalgesia to mechanical and cooling stimuli returned. At this time, her ongoing level of pain also increased substantially. Injection-of phenylephrine at the control site in this patient evoked moderate pain of shorter duration. Only brief, mild pain sensations and no hyperalgesia were evoked by the phenylephrine injections into the control subjects.

In summary, topical application of clonidine significantly reduced mechanical and cold hyperalgesia at the site of drug administration in patients with SMP. The decrease in hyperalgesia was not due to a local anesthetic effect since touch detection thresholds were not altered by the clonidine treatment in the patients and in the control subject. There was no change in the hyperalgesia outside the area of drug application in patients with a large zone of hyperalgesia. In addition, the ongoing, stimulus-independent pain was not affected by the clonidine patches in these patient. Clonidine had little effect on pain or hyperalgesia in the patients whose pain was independent of the sympathetics (cases 5 and 6). Local administration of adrenergic agonists into the affected skin in patients with SMP evoked unusually sustained, intense pain compared to the pain evoked in normal subjects. These observations indicate an important role of peripheral $\alpha_1$-adrenergic receptors in SMP.

Based on the above examples, it is clear that any α-adrenergic antagonist, α-1-adrenergic antagonist, α2 adrenergic agonist, or other drug that depletes sympathetic norepinephrine, for example, bretylium, reserpine, phenoxybenzamine, or guanethidine, will relieve SMP using the method according to the present invention. Further, due to the number of side-effects and short effective half-lives associated with these compounds, topical administration of these compounds is preferred.

Modifications and variations of the compositions and methods of use thereof of the present invention will be obvious to those skilled in the art from the foregoing detailed description. Such modifications and variations are intended to come within the scope of the appended claims.

I claim:

1. A method of treating sympathetically maintained pain in peripheral tissues comprising topically administering to a patient having sympathetically maintained pain at a peripheral site where the pain originates, wherein the sympathetically maintained pain can be diagnosed by local anesthetic blockade of the appropriate sympathetic ganglion or adrenergic blockade via intravenous administration of phentolamine, and rekindled by intradermal injection of norepinephrine, an effective amount of a compound other than guanethidine that depletes norepinephrine or blocks synthesis or release of norepinephrine at the sympathetic terminals in a pharmaceutically acceptable carrier for topical application selected from the group consisting of a lotion, ointment, solution, and transdermal patch to cause measurable relief from the sympathetically maintained pain.

2. The method of claim 1 wherein the compound is administered in a transdermal patch.

3. The method of claim 1 wherein the compound is selected from the group consisting of bethanidine, guanclofine, guanoxan, guanazodine, guanoxyfen, guanocline, guanoctine, and guanadrel.

4. The method of claim 1 wherein the compound is selected from the group consisting of guanoxabenz, and guanoclor.

5. The method of claim 1 wherein the compound is selected from the group consisting of debrisoquin and guanisoquin.

6. The method of claim 1 wherein the compound is selected from the group consisting of solypertine, naftopidil, saterinone, trazodone, nefazodone, tiospirone, 3-[2-[4-(o-methoxyphenyl)-1-piperazinyl]ethyl]-2,4(1H,3H)-quinazolinedione monohydrochloride, and 1-[2-ethoxy-2-(3'-pyridyl)ethyl]-4-(2'-methoxy-phenyl)piperazine.

7. The method of claim 1 wherein the compound is a Rauwolfia alkaloid.

8. The method of claim 1 wherein the compound is an ergot alkaloid.

9. The method of claim 1 wherein the compound is the compound 5-n-butylpicolinic acid hydrazide.

10. The method of claim 1 wherein the compound is selected from the group consisting of 1-(3-mercapto-2-methyl-1-oxopropyl)-L-proline and 1-(2-mercaptacetyl)-L-proline.

11. The method of claim 1 wherein the compound is bretylium.

12. The method of claim 1 wherein the compound is methylapogalanthamine.

* * * * *